United States Patent [19]

Bonte et al.

[11] Patent Number: 5,510,113
[45] Date of Patent: Apr. 23, 1996

[54] COMPOSITION BASED ON HYDRATED LIPIDIC LAMELAR PHASES OR ON LIPOSOMES CONTAINING AT LEAST ONE DERIVATIVE OF LABDANE, OR A PLANT EXTRACT CONTAINING IT; COSMETIC OR PHARMACEUTICAL, PARTICULARLY DERMATOLOGICAL COMPOSITION CONTAINING IT

[75] Inventors: Frederic Bonte; Alain Meybeck, both of Courbevoie; Christian Marechal, Paris, all of France

[73] Assignee: LVMH Recherche, Nanterre, France

[21] Appl. No.: 323,077

[22] Filed: Oct. 14, 1994

Related U.S. Application Data

[62] Division of Ser. No. 768,292, Dec. 12, 1991, Pat. No. 5,384,126.

[30] Foreign Application Priority Data

Aug. 17, 1989 [FR] France ................................ 89 10986

[51] Int. Cl.⁶ .................................................. A61K 9/127
[52] U.S. Cl. .......................... 424/450; 424/70.6; 514/880; 514/881
[58] Field of Search ................................... 424/450, 70.1, 424/70.6; 514/880, 881

[56] References Cited

U.S. PATENT DOCUMENTS

| | | | |
|---|---|---|---|
| 4,118,508 | 10/1978 | Bhat | 424/283 |
| 4,476,140 | 10/1984 | Sears | 424/283 |
| 5,017,368 | 5/1991 | Sugiyama | 424/70 |
| 5,141,942 | 8/1992 | Lal | 514/267 |

OTHER PUBLICATIONS

Mezei. Life Sciences 26, 1473 1980.

*Primary Examiner*—Gollamudi S. Kishore
*Attorney, Agent, or Firm*—Rosen, Dainow & Jacobs

[57] ABSTRACT

The present invention relates to a novel composition based on hydrated lipidic lamelar phases or on liposomes and to a cosmetic or pharmaceutical, particularly dermatological composition incorporating it. The hydrated lipidic lamelar phases or the liposomes contain at least in part a derivative of labdane, or a plant extract containing it. The invention reduces hair drop and promotes regrowth of hair and also prevents gray hair from appearing and provides a treatment for gray hair.

22 Claims, 1 Drawing Sheet

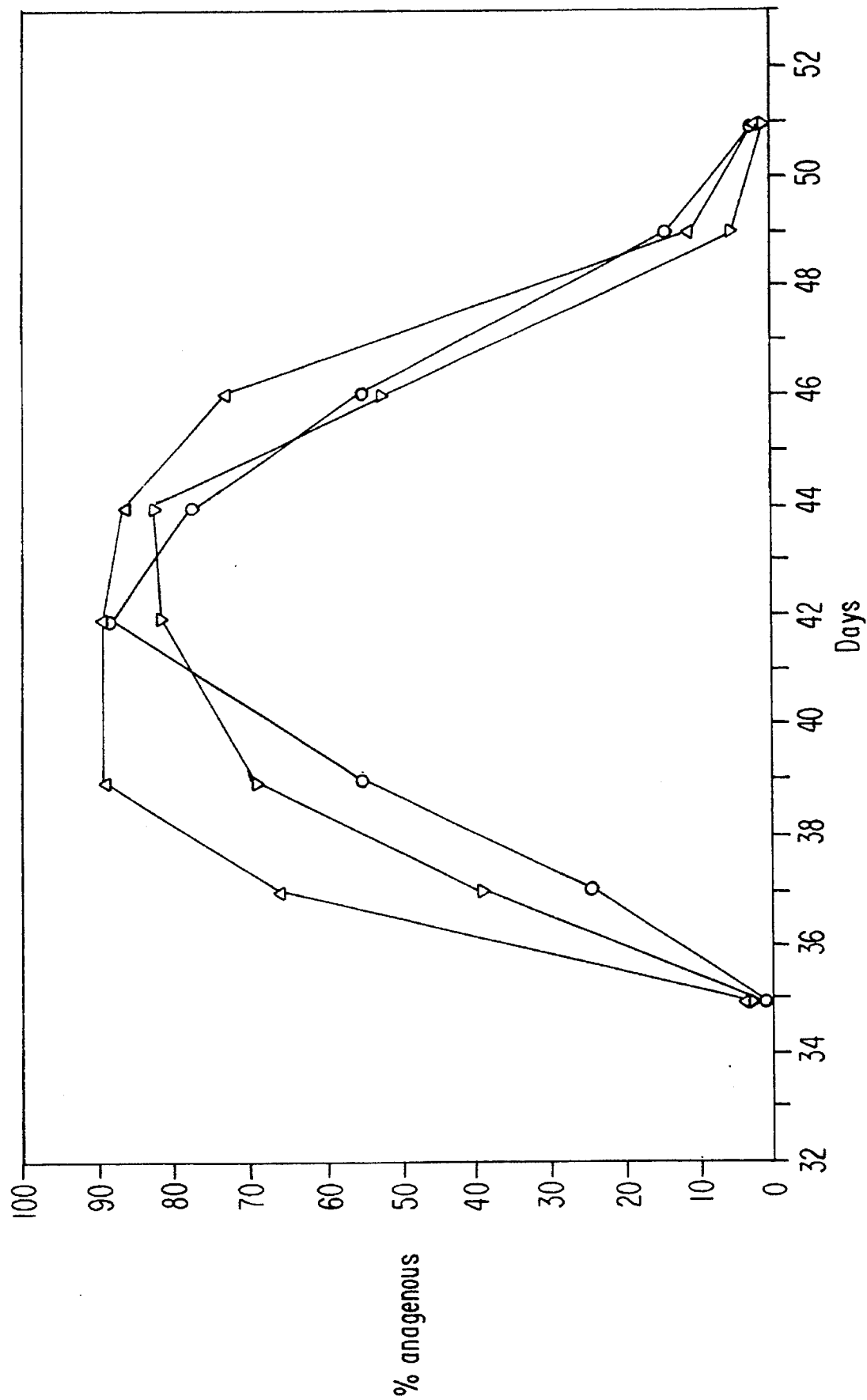

COMPOSITION BASED ON HYDRATED LIPIDIC LAMELAR PHASES OR ON LIPOSOMES CONTAINING AT LEAST ONE DERIVATIVE OF LABDANE, OR A PLANT EXTRACT CONTAINING IT; COSMETIC OR PHARMACEUTICAL, PARTICULARLY DERMATOLOGICAL COMPOSITION CONTAINING IT

This application is a division of application Ser. No. 07/768,292, filed Dec. 12, 1991, now U.S. Pat. No. 5,384,126.

The present invention relates to compositions based on hydrated lipidic lamelar phases or on liposomes containing at least one derivative of labdane, in particular a labd-14-ene, or a plant extract containing it, intended for the preparation of cosmetic or pharmaceutical, particularly dermatological compositions.

Labdanes, and in particular their unsaturated derivatives in 14 position, called labd-14-enes, are diterpenes which are fairly widely distributed in nature.

They are found in particular in different varieties of conifers (particularly pines), tobaccos, cistuses (in particular *Cistus ladaniferus, Cistus laurifolius*), and Coleus (particularly *Coleus forskohlii*).

*Coleus forskohlii* represents one of the two hundred or so known species of Coleus, belonging to the family of Labiaceae and which are found in the tropical and subtropical regions of Asia, Africa, Australia and the Pacific islands. About nine species are catalogued in India. The ten principal varieties of Coleus are catalogued in Indian dictionaries and in particular "The Wealth of India," a dictionary of Indian Raw Materials and Industrial Products, Raw Materials, volume II, Dehli 1950, pages 308–309; the book entitled Indian Materia Medica by Dr. K. M. Nadkarni's, third edition revised and completed by A. K. Nadkarni in two volumes, Volume I, page 372; the book entitled "The Flora of British India" by Sir J. D. Hooker, C. B., K. C., S. I. Volume IV entitled "Asclepiadae to Amarantaceae, pages 624 to 627.

The labdane derivatives to which the present invention refers are in particular derivatives of general formula:

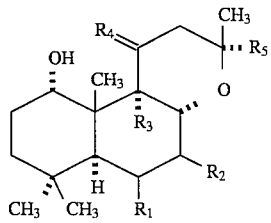

(I)

in which:

$R_1$ to $R_2$ are identical or different and each represent a hydroxy group or a —O—$COR_6$ group in which $R_6$ represents an alkyl, alcoxy or alkenyl radical possibly substituted, particularly by one or more hydroxy or amino groups, $R_3$ represents an atom of hydrogen or a hydroxy group, $R_4$ represents an atom of oxygen or the assembly

$R_5$ represents an ethyl or vinyl radical.

Several derivatives of labdane responding to the above formula have been extracted from various plants and in particular from the plant *Coleus forskolii*. Particular reference will be made to documents FR-2 336 138, FR-2 364 211 and EP-A-1-O 243 646 which describe forskoline (compound of formula I in which $R_1$=$R_3$=OH; $R_2$=OCOCH$_3$; $R_4$=O; $R_5$=CH=CH$_2$), 9-deoxyforskoline (compound of formula I in which $R_1$=OH, $R_2$=OCOCH$_3$; $R_3$=H; $R_4$=O; $R_5$=CH=CH$_2$) and coleforsine (compound of formula I in which $R_2$=$R_3$=OH; $R_1$=OCOCH$_3$; $R_4$=O; $R_5$=CH=CH$_2$).

Other derivatives of labdane responding to the above formula have been prepared by synthesis. Particular reference will be made to the following documents: FR-2 372 822; S. V. BHAT et al., J. Chem. Soc., Perkin Trans. 1982, volume 1, page 767; S. V. BHAT et al., J. Med. Chem. 1983, volume 26, pages 486–492; EP-A-252 482; EP-A-217 372; E. SEGUIN et al., Planta Medica, 1938, volume 54 No. 1, pages 4–6.

These documents disclose, in addition, that these compounds present certain pharmacological properties and in particular a hypotensive and calming activity on the central nervous system.

Furthermore, document EP-A-O 120 165 describes the local use of associations comprising a β-stimulant and an $α_2$-inhibitor, for the treatment of fatty weight. This document cites forskoline by way of example of β-stimulant.

The present invention has for its object to solve the new technical problem consisting in the preparation of a novel formulation of a cosmetic or pharmaceutical, particularly dermatological composition, comprising as active ingredient a labdane or a plant extract containing it and making it possible to potentialize the activity of this ingredient, in particular with respect to the stimulation of regrowth of hair or the reduction in hair loss.

In fact, it has been discovered in totally unexpected manner, and this constitutes the basis of the present invention, that the labdines or the plant extracts containing them, presented an activity stimulating the regrowth of hair and slowing down hair loss. In addition, it has been discovered that this activity, which remains weak for certain of these compounds, may be very considerably potentialized by their incorporation in hydrated lipidic lamelar phases or in liposomes.

In this way, according to a first aspect, the present invention concerns a composition based on hydrated lipidic lamelar phases, notably liposomes, characterized in that said hydrated lipidic lamelar phases, notably liposomes contain at least in part a derivative of labdane, of formula I hereinafter, and/or a plant extract containing it.

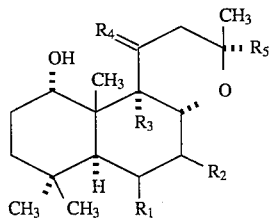

(I)

in which:

$R_1$ and $R_2$ are identical or different and each represent a hydroxy group or a —O—CO—$R_6$— group in which $R_6$ represents an alkyl radical having from 1 to 7 atoms of carbon, alkoxy radical having from 1 to 7 atoms of carbon or alkenyl radical having from 1 to 7 atoms of carbon, possibly substituted by one or more hydroxy or

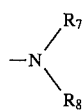

groups in which $R_7$ and $R_8$ each represent an atom of hydrogen, an alkyl radical having from 1 to 4 atoms of carbon such as methyl or ethyl or represent together and with the atom of nitrogen a heterocyclic radical such as piperidino, morpholino, N'-methyl-piperazino;

$R_3$ represents an atom of hydrogen or a hydroxy group;

$R_4$ represents an atom of oxygen or the assembly

$R_5$ represents an ethyl or vinyl radical.

According to a particular characteristic, the labdane derivative is a compound of formula (I) mentioned above in which:

$R_1$ represents the hydroxy group;

$R_2$ represents a hydroxy group or a —O—CO—$R_6$ group in which $R_6$ represents an alkyl radical having from 1 to 4 atoms of carbon, an alkoxy radical having from 1 to 4 atoms of carbon or an alkenyl radical having 1 to 4 atoms of carbon, possibly substituted by one or two hydroxy groups or, at one end of chain, by a

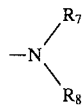

group in which $R_7$ and $R_8$ each represent a methyl or ethyl radical or represent together and with the atom of nitrogen a heterocyclic radical such as piperidino, morpholino, N'-methyl-piperazino;

$R_3$ represents the hydroxy group;

$R_4$ represents an atom of oxygen;

$R_5$ represents the vinyl radical.

The alkyl radicals, represented by $R_6$, $R_7$ and $R_8$ in the above formulae may be with linear, branched or cyclic chain.

An alkyl radical $C_1$–$C_7$ is for example a methyl, ethyl, propyl, isopropyl, cyclopropyl, isobutyl, butyl, pentyl, neopentyl, preferably methyl, ethyl or propyl radical.

On the other hand, the alkoxy and alkenyl radicals represented by $R_6$ in the above formulae may also be with linear, branched or cyclic chain.

An alkoxy group with $C_1$–$C_7$ is for example a methoxy, ethoxy, propoxy, isopropoxy, cyclopropoxy, butoxy, pentoxy, preferably methoxy, ethoxy or propoxy group.

An alkenyl group with $C_1$–$C_7$ is for example a vinyl, allyl, isopropenyl, butenyl, pentenyl, cyclohexenyl group.

This labdane derivative is advantageously chosen from the following compounds:

n° 1: forskoline n° 2: 7-O-deacetyl-forskoline n° 3: coleforsine n° 4: 7-O-deacetyl-7-β-O-propanoyl-forskoline n° 5: 7-O-deacetyl-7-β-O-(ethoxycarbonyl)-forskoline n° 6: 7-O-deacetyl-7-3-O-(propoxycarbonyl)-forskoline n° 7: 7-O-deacetyl-7-β-O-(2,3-dihydroxy-propanoyl)-forskoline n° 8: 7-O-deacetyl-7-β-O-(3-methyl-2-butenoyl)-forskoline n° 9: 7,O-deacetyl-7-β-O-[4-(N'-methyl-piperazino)-butanoylΩ-forskoline n° 10: 7-O-deacetyl-7-β-O-(4-morpholino-butanoyl)-forskoline n° 11: 6-β-O-[3-piperidino-propanoylΩ-forskoline n° 12: 6-β-O-(piperidino-acetyl)-forskoline These labdane derivatives are compounds of formula (I) above in which $R_3$=OH, $R_4$=O, $R_5$=CH=CH$_3$ and $R_1$ and $R_2$ have the significances figuring in Table I hereinbelow:

TABLE I

| n° | $R_1$ | $R_2$ |
|---|---|---|
| 1 | OH | OCOMe |
| 2 | OH | OH |
| 3 | OCOMe | OH |
| 4 | OH | OCOEt |
| 5 | OH | OCOOEt |
| 6 | OH | OCOOPr |
| 7 | OH | OCO—CH(OH)—CH$_2$OH |
| 8 | OH | O—CO—CH=C(CH$_3$)$_2$ |
| 9 | OH | O—CO—(CH$_2$)$_3$—N⟨  ⟩N—CH$_3$ |
| 10 | OH | O—CO—(CH$_2$)$_3$—N⟨  ⟩O |
| 11 | OCO—(CH$_2$)—N⟨  ⟩ | OCOMe |

TABLE I-continued

| n° | R₁ | R₂ |
|---|---|---|
| 12 | OCO—CH₂—N⟨hexagon⟩ | OCOMe |

According to another embodiment of the invention, for preparing such a composition, an extract containing a labdane derivative as defined previously is used, which is for example an extract of Coleus, in particular an extract of *Coleus forskolii,* preferably an extract of roots of the plant Coleus.

Advantageously, it is question of an organic extract of Coleus, particularly of roots of Coleus, preferably obtained by a process comprising at least one step of extraction with a solvent selected from the group constituted by ethyl acetate, methanol, ethanol and dichloromethane.

However, use may be made, as solvent, of organic solvents such as aromatic hydroacarbons, dialkylics, halogenated aliphatic and aromatic hydrocarbons, dialkylic ethers, dialkylketones, alkanols, carboxylic acids and their esters; or other solvents such as for example dimethylformamide, dioxane, tetrahydrofurane and dimethylsulfoxide.

Among the solvents mentioned above, preferred solvents are benzene, toluene or xylene, methylene chloride, chloroform, ethyl acetate, methanol or ethanol.

The ratio of the plant matter with respect to the extraction agent is not critical and will generally be included between 1:5 and 1:20 parts by weight, and preferably 1:10 parts by weight about.

Extraction is effected at temperatures included between ambient temperature and the boiling point of the solvent used for extraction.

A particularly advantageous technique of extraction is the so-called technique of extraction employing Soxhlet. It may be advantageous, and in certain cases necessary, to evaporate the solvent, for example by lyophilization, and to take up the crude extracts with a view to a purification.

Within the framework of the present invention, extraction by alcohol is particularly interesting, particularly at the end of procedure for obtaining the extract due to the usually hardly toxic character of the alcohols. A particularly advantageous alcohol is ethanol.

Another particularly interesting solvent is ethyl acetate because it furnishes an extract rich in labd-14-ene derivative.

Particular variants of process are also described in the prior art, in particular in the documents recalled in the preamble of the present specification.

The term "lipidic" in the expression "lipidic lamelar phases" covers all the substances comprising a so-called fatty carbon chain, generally comprising more than 5 atoms of carbon, this substance usually being called "lipid".

According to the invention, for forming the lipidic lamelot phases, notably liposomes, use is made by way of lipid of amphiphilic lipids, i.e. constituted by molecules presenting a hydrophilic group which is equally well ionic or non-ionic and a lipophilic group, these amphiphilic lipids being capable of forming lipidic lamelar phases, notably liposomes, in the presence of an aqueous phase, depending on the quantity of water in the mixture.

In particular, among these lipids, mention may be made of: the phospholipids, phosphoaminolipids, glycolipids, polyoxyethylenated fatty alcohols, the possibly polyoxyethylenated polyol esters. Such substances are for example constituted by an egg or soya lecithin, a phosphatidylserine, a sphyngomyeline, a cerebroside or an oxyethylenated polyglycerol stearate.

According to the invention, a lipidic mixture is preferably used, constituted by at least one amphiphilic lipid and at least one hydrophobic lipid such as sterol, like cholesterol or β-sitosterol. The quantity, expressed in mols, of hydrophobic lipid must generally not be greater than the quantity of amphiphilic lipid, and preferably, it must not be greater than 0.5 times this quantity.

The incorporation in hydrated lipidic lamelar phases, notably liposomes, of the compounds or extracts containing these compounds, used in accordance with the present invention, may be effected in accordance with known techniques of preparation, described for example in U.S. Pat. No. 4,508,703, and possibly in combination with U.S. Pat. No. 4,621,023.

According to a second aspect, the present invention concerns a cosmetic or pharmaceutical, particularly dermatological composition, intended in particular to promote regrowth of hair or to reduce hair loss or to promote pigmentation of the epidermis or to prevent gray hair appearing or for treating gray hair, characterized in that it comprises, by way of active ingredient, at least one derivative of labdane, of formula I mentioned above, and/or an extract of plants containing it, at least partly incorporated in hydrated lipidic lamelar phases, notably liposomes.

The cosmetic or pharmaceutical, particularly dermatological compositions according to the present invention will generally be produced from the compositions based on hydrated lipidic lamelar phases, notably liposomes described hereinbefore.

The concentration of labdane derivative or of extract containing it, incorporated at least in part in hydrated lipidic lamelar phases, notably liposomes, will preferably be included between 0.0001% and 1% by weight, preferably still between 0.01% and 0.1% by weight, with respect to the total weight of the cosmetic or pharmaceutical composition.

These proportions are understood to be by dry weight when it is question of plant extracts.

According to a variant embodiment, a cosmetic or pharmaceutical, particularly dermatological composition according to the invention comprises in addition at least one other active substance, at an efficient concentration, selected from xanthines, vitamins, particularly vitamin B's, tyrosine or its derivatives such as for example glucose tyrosinate, quinine or its derivatives, rubefacients such as methyl nicotinate, a supernatant of culture of fibroblasts of papillae, as defined in document EP-A-272 920, keratin hydrolysates, oligo-elements such as zinc, selenium, copper, 5-α-reductase inhibitors such as: progesterone, cyproterone acetate, Minoxidil, azelaic acid and its derivatives, a 4-methyl-4-azasteroid, in particular 17-β-N,N-diethyl-carbamoyl- 4-methyl-4-aza-5-α-androstan-3-one, or an extract of Serenoa repens, said active substance possibly being incorporated at least in part in said hydrated lipidic lamelar phases, notably liposomes.

The cosmetic compositions according to the present invention may be applied topically to promote regrowth of hair, to reduce hair loss, or to promote pigmentation of the epidermis or prevent gray hair from appearing or for treating gray hair, in particular in compositions in the form of creams, gels or lotions intended for topical application on the hair.

Under this aspect, the present invention also provides a process for treating the hair intended in particular to promote regrowth thereof and to reduce drop thereof or to promote pigmentation of the epidermis or prevent gray hair from appearing or for treating gray hair, characterized in that it comprises the application, in an efficient quantity to produce the effect of regrowth of the hair or for reducing loss thereof, to promote pigmentation of the epidermis or prevent gray hair from appearing or to treat gray hair, of at least one composition based on hydrated lipidic lamelar phases, notably liposomes, as defined previously, possibly in association with a pharmaceutically or cosmetically acceptable excipient, vehicle or support.

It should be noted that the expression "at least partly incorporated in hydrated lipidic lamelar phases, notably liposomes" is understood to mean in the present description and in the claims, that the derivative of labdane or the extract of plants containing it is combined with hydrated lipidic lamelar phases, notably liposomes, whatever the form of this combination.

However, it is clear that a preferred combination according to the invention resides in the incorporation, or even the encapsulation, in the hydrated lipidic lamelar phases, notably liposomes. However, it is not necessary that the whole of the active principle be incorporated or encapsulated in order to obtain the desired effect.

According to another aspect, the invention further provides a process for manufacturing a cosmetic or pharmaceutical, particularly dermatological composition intended to promote regrowth of hair or to delay hair loss, to promote pigmentation of the epidermis or to prevent gray hair from appearing or to treat gray hair, characterized in that it comprises the incorporation of at least one labdane and/or a plant extract containing it, at least in part in hydrated lipidic lamellar phases, notably liposomes, then the mixture thereof in a pharmaceutically or cosmetically acceptable excipient, vehicle or support.

Under this latter aspect, the invention concerns the use of a composition based on hydrated lipidic lamelar phases, notably liposomes such as defined hereinabove for the preparation of a cosmetic or pharmaceutical, particularly dermatological composition, intended for the treatment of hair, particularly for promoting regrowth of the hair or for reducing hair loss and for preventing gray hair from appearing or for treating gray hair.

Other purposes, characteristics and advantages of the invention will appear more clearly upon reading the following explanatory description made with reference to several Examples given solely by way of illustration and which consequently in no way limit the scope of the invention.

In the Examples, the percentages are expressed by weight, unless indicated to the contrary.

When it is question of plant extracts, the weights indicated are dry weights unless indicated to the contrary.

BRIEF DESCRIPTION OF THE DRAWING

The accompanying single FIGURE reports test results of the products of the present invention on the pilary cycle of Sprague-Dawley rats with the percentage of hairs in anagenous phase comprising the Y-axis as a function of the number of days on the X-axis, as reported in detail in Example 10.

EXAMPLE 1

Preparation of a suspension of liposomes containing a labd-14-ene derivative

In 25 ml of a mixture of dichloromethane and of methanol in volumetric proportion 4:1, are dissolved 0.398 g of soya lecithin and 0.002 g of forskoline ($1\alpha$, $6\beta$, 9 $\alpha$-trihydroxy-$7\beta$-acetoxy-8,13-epoxy-labd-14-en-11-one).

The solution is evaporated in a rotating flask under reduced pressure at about 45° C.

The lipidic film obtained is taken up with stirring in about 19.6 ml of aqueous solution constituted by a phosphate PBS buffer.

A suspension of lipidic vesicles or liposomes is obtained, which is then treated with ultra-sounds for 15 minutes at 4° C. with a power of 150 W.

A suspension of liposomes is thus obtained, of substantially homogeneous size, of the order of 139 nm. This suspension contains about 0.01% of forskoline, incorporated in the lipidic phase of the liposomes.

If desired, this suspension may be gelified, for example by mixing it with an equivalent volume of a gel of Carbopol 940® prepared in conventional manner.

EXAMPLE 2

Obtaining of an extract of Coleus from *Coleus forskolii*

60 g of dried, ground roots of *Coleus forskolii* are extracted with Soxhlet with 600 ml of solvent. Extraction is effected at boiling temperature of the solvent with an ever-renewed solvent.

The mean yield of extraction is as follows, expressed in dry weight:
a) Ethanol/water mixture (80/20 v/v): about 9.2 to 9.5 g (extract 2A)
b) Ethyl acetate: about 1.5 g (extract 2B)
c) Dichloromethane: about 4 g (extract 2C).

EXAMPLE 3

Incorporation of an extract of *Coleus forskolii* in hydrated lipidic lamelar phases or in liposomes An extract of *Coleus forskolii* obtained in accordance with Example 2 is incorporated in hydrated lipidic lamelar phases or in liposomes in accordance with the technique of preparation described in Example 1.

The preparation of the liposomes is for example as follows:

The following are weighed:

| | |
|---|---|
| soya lecithin | 0.9 g |
| β-sitosterol | 0.1 g |
| lyophilized Coleus extract (extract 2B) | 0.025 g |

These constituents are dissolved in a mixture constituted by 100 ml of dichloromethane and 25 ml of methanol.

The mixture thus obtained is evaporated in a rotating flask at a temperature of 45° C. under reduced pressure.

The lipidic film thus obtained is then taken up and dispersed with stirring in distilled water qsp 50 g, at ambient temperature for 2 hours.

The suspension of lipidic vesicles obtained is then homogenized by an ultra-sound treatment for 30 minutes at 4° C., at a power of 150 W.

The mean size of the liposomes thus obtained is about 212 nm.

This suspension is then gelified by mixing it with 50 g of Carbopol 940® gel at 1.25% prepared separately in conventional manner. About 100 g are thus obtained of a gelified suspension of liposomes encapsulating the extract of *Coleus forskolii*, whose concentration is about 0.025% with respect to the total weight of the suspension.

EXAMPLES 4 TO 9

By following the experimental process described in Example 1, suspensions of liposomes were prepared from the following compositions:

Example 4:

| | |
|---|---|
| soya lecithin | 2 g |
| β-sitosterol | 0.05 g |
| Coleus extract (extract 2B) | 0.01 g |
| distilled water, qsp | 50 g |

Example 5

| | |
|---|---|
| lecithin of egg | 1.8 g |
| cholesterol | 0.1 g |
| extract of Coleus (extract 2A) | 0.02 g |
| distilled water, qsp | 50 g |

Example 6

| | |
|---|---|
| lecithin of soya | 2 g |
| extract of Coleus (extract 2C) | 0.035 g |
| distilled water, qsp | 50 g |

Example 7

| | |
|---|---|
| lecithin of soya | 2 g |
| β-sitosterol | 0.1 g |
| extract of Coleus (extract 2B) | 0.03 g |
| distilled water, qsp | 50 g |

Example 8

| | |
|---|---|
| lecithin of soya | 2 g |
| progesterone | 0.001 g |
| extract of Coleus (extract 2A) | 0.0275 g |
| distilled water, qsp | 45 g |

Example 9

| | |
|---|---|
| lecithin of soya | 2 g |
| extract of Coleus (extract 2C) | 0.025 g |
| extract of Serenoa repens | 0.01 g |
| distilled water | 50 g |

EXAMPLE 10

Evidencing of an hair loss preventing activity on the growth of the hair

The hair loss preventing activity on the growth of the hair is evidenced by studying the activity of the products according to the invention on the pilary cycle of Sprague Dawley rats aged 23 days. The rats are shaved, in the lower part of their back, on the 24th day.

From the 25th day and up to the 65th day, 6 days out of 7, the products to be tested are then applied at a dose ranging from 0.5 ml to 2 ml as a function of the weight gain of the animals.

At substantially regular intervals of time (every 3 days about), a small tuft of at least 10 hairs is removed, with tweezers, on the left-hand side of the animal; at the level of the flank.

The percentage of hairs in anagenous phase (phase of growth) is then counted as a function of time. Identification of the hairs in anagenous phase is effected by microscopic observation of the lower end of the hair. The base of the hairs in anagenous phase is fine, as the living part has remained in the dermis, whilst the base of the hairs in telogenous phase (rest phase) is in club form. The hairs in catagenous phase (intermediate phase of regression) are always very few.

The study is made on 30 rats distributed in 3 batches of 10 animals. The first batch receives the product of Example 3. The second receives an alcoholic solution of the same extract of Coleus at the same concentration of 0.025%. The third batch is the control batch receiving no product.

The results of this trichokinetic study are given in the accompanying single FIGURE.

In this FIGURE, the percentage of hairs in anagenous phase is plotted on the y-axis and the number of days on the x-axis.

The curve joining the triangles whose apex is directed upwardly corresponds to the results obtained with liposomes incorporating 0.025% of extract of Coleus, and prepared according to Example 3.

The curve joining the triangles whose apex is directed downwardly corresponds to the results obtained with the control batch.

The curve joining the circles corresponds to the results obtained with an extract of Coleus in alcohol, in the free state, at the same proportion of 0.025% by weight, with respect to the total weight of the composition.

It will be observed that the number of hairs in anagenous phase increases much more rapidly in the batch receiving the extract of Coleus in liposomes according to the invention, than in the one receiving the alcoholic solution of extract of Coleus (respectively 65% and 25% on day 37). It will also be observed that the anagenous phase extends longer.

On the other hand, if the curve corresponding to the alcoholic solution of extract of Coleus is compared with the control curve, no really significant difference is observed.

In this way, it is clear that the extracts of Coleus incorporated in the liposomes, according to the invention, by the extension of the duration of the anagenous phase, very clearly slow down hair loss and promote regrowth thereof.

EXAMPLE 11

Measurement of the pigmenting activity of an extract of *Coleus forskohlii* incorporated in liposomes on the cutaneous pigmentation in the guinea pig Protocol:

The study was made on a batch of 10 three-coloured guinea pigs.

Before and during the experimentation, the right and left flanks of the guinea pigs were carefully shaved, every day for the first 5 days (period of exposure to U.V.), then every 2 days until the end of the study.

For each animal, there are determined on each flank comparably pigmented marks, most often of light brown appearance. On one of the two flanks taken at random, about 0.5 g of product to be tested or of control product, depending on the batch, is applied 10 mins. before exposure to ultraviolet rays, the other flank being exposed "bare" by way of control.

The application of the products to be tested is effected as from the first day of exposure until the animal is sacrificed.

Exposure to ultraviolet radiation is effected by means of a solar simulator delivering 86% of U.V.A. and 14% U.V.B during the first 5 days of the experiment, at a rate of 5 mins. the first day, 10 mins. the second day, 15 mins. the third day and 20 mins. the fourth and fifth days.

The animals are sacrificed 12 days after the last exposure, and a cutaneous biopsy is effected.

A fragment of skin is thus removed from the non-treated but exposed flank as well as from the other treated and exposed flank.

A histological examination is then made of the cutaneous fragments.

This examination comprises: on the one hand, the study of the melanogenesis by the Argentaffine de Fontana method on sections of 4>m (Techniques d'histologie, Professor Chevreau, Ed. Maloine, 1977, page 157), on the other hand, the assessment of the thickness of the epidermis on sections of 4>m coloured in accordance with the trichomic method of Masson.

The study of the thickness of the epidermis and of the intensity of the melanogenesis makes it possible to assess a tanning effect or more exactly the activation of the process of melanogenesis.

To study the melanogenesis, two zones taken at random from a pigmented mark are examined, in which 25 malpigian cells are noted and among the latter the "activated" melanocytes are counted, i.e. containing melanine in a cluster. The activation of the process of melanogenesis is then expressed in percentage of activated cells from the average of these two values.

On these same zones, the quantity of melanine in the other layers of the epidermis is examined and this quantity is assessed overall in a scale with five values varying from 0 to 4 depending on whether the quantity of melanine formed is zero, low, average, large or very large.

Table I shows the results of the histological study giving the percentage of activation and making it possible to assess the variations in the quantity of melanine formed (average values on the scale defined hereinabove), of the thickness of the epidermis (expressed in >m).

The product tested is constituted by an extract of Coleus with ethyl acetate according to Example 2b, incorporated in liposomes according to Example 3, but titrating 0.0284% of Coleus extract instead of 0.025%.

TABLE I

|  | Control flank | Treated flank |
| --- | --- | --- |
| % Activation | 33.40 | 85.30 |
| Quantity of metanine | 0.16 | 2.39 |
| Thickening of the epidermis in >m | 8.32 | 14.10 |

From Table I it may be ascertained that the extract of Coleus incorporated in liposomes according to the invention is active on melanogenesis. A reading of the histological sections of the treated flanks shows a very high rate of activated melanocytes presenting rhizomic forms, and a considerable migration of the grains of melanines in the epidermis.

These results therefore clearly confirm the activity of the extracts of Coleus incorporated in liposomes according to the invention on the activation of the melanocytes.

Various examples of formulation of cosmetic or pharmaceutical compositions promoting regrowth of the hair and/or reducing hair drop and/or preventing gray hair from appearing or for treating gray hair, will be given hereinafter. The hydrosoluble constituents may advantageously be dissolved in the aqueous phase in which the lipidic powder is dispersed, as indicated in Example 3. For example, these constituents may be incorporated, at least in part, in the liposomes.

EXAMPLE 12

Lotion reducing hair loss

| Suspension of liposomes according to Example 4 | 50 g |
| --- | --- |
| Carbopol 940 ® | 0.03 g |
| distilled water, qsp | 100 ml |

This lotion is applied on the scalp twice a day for 6 months.

EXAMPLE 13

Anti-hair drop lotion

| Suspension of liposomes according to Example 5 | 50 g |
| --- | --- |
| Carbopol 940 ® | 0.03 g |
| panthenol | 0.1 g |
| keratin hydrolysat | 0.2 g |
| hydrosoluble perfume | 0.1 g |
| distilled water, qsp | 100 ml |

This lotion is applied on the scalp twice a day for 6 months.

EXAMPLE 14

Lotion for stimulating the dermal papilla

| Suspension of liposomes according to Example 6 | 50 g |
| --- | --- |
| Carbopol 940 ® | 0.04 g |
| Phytantriol ® | 0.1 g |
| conserving agents | 0.05 g |
| protein-zinc complex | 0.1 g |
| water, qsp | 100 ml |

This lotion is applied on the scalp, over the areas where the hair has fallen, 5 days out of 7, in a cure of 6 months. This application is followed by a slight massage.

EXAMPLE 15

Lotion promoting regrowth of the hair and preventing gray hair from appearing

| Suspension of liposomes according to Example 7 | 50 g |
| --- | --- |
| Carbopol 940 ® | 0.05 |
| glucose tyrosinate | 0.05 |
| complex of oligo-elements | 0.1 |

-continued

| | |
|---|---|
| theophylline | 0.01 |
| conserving agents | 0.05 |
| distilled water, qsp | 100 ml |

This lotion is applied in the evening on the scalp over the graying areas and the zones where the hair has fallen, in a cure of 4 months.

EXAMPLE 16

Hair loss preventing gel

| | |
|---|---|
| Suspension of liposomes according to Example 8 | 45 g |
| perfume | 0.1 g |
| Carbopol 940 ® gel at 1.5% | 50 g |
| distilled water, qsp | 100 g |

Apply this gel, preferably after a shampoo, twice a week, in a cure of 2 months.

EXAMPLE 17

Hair loss preventing gel against seborrheic alopecia

| | |
|---|---|
| Suspension of liposomes according to Example 9 | 50 g |
| perfume | 0.1 |
| protein-zinc complex | 0.05 |
| Carbopol gel at 1.5% | 45 g |
| water, qsp | 100 g |

This gel is preferably applied every evening over the areas of drop, in a cure of 4 months.

EXAMPLE 18

Lotion reducing hair loss preventing

| | |
|---|---|
| Suspension of liposomes according to Example 1 | 20 g |
| Carbopol 940 ® | 0.03 g |
| distilled water, qsp | 100 ml |

EXAMPLE 19

Tanning gel

| | |
|---|---|
| Suspension of liposomes (non-gelified) according to Example 3 | 50 g |
| Carbopol 940 ® | 1.25 g |
| hydrosoluble solar filter | 6 g |
| distilled water, qsp | 100 g |

EXAMPLE 20

Lotion promoting regrowth of the hair

| | |
|---|---|
| Suspension of liposomes according to Example 7 but containing in the aqueous phase human keratin hydrolysate at a concentration of 5% | 50 g |
| Carbopol 940 ® | 0.05 g |
| Complex of oligo-elements | 0.1 g |
| conserving agent | 0.05 g |
| distilled water, qsp | 100 ml |

The suspension of liposomes according to Example 7 containing in the aqueous phase human keratin hydrolysate at 5%, is prepared in accordance with Example 3 except that the lipidic film is taken up in an aqueous solution containing 5% of human keratin hydrolysate.

This solution is applied in the evenings on the scalp in the areas of hair loss, in a cure of 4 months.

As it is well known to those skilled in the art, liposomes represent a particular embodiment of hydrated lipidic lamelar phases. Thus, according to the invention, the hydrated lipidic lamelar phases are in a specific embodiment in the form of liposomes.

We claim:

1. A method for promoting hair pigmentation, comprising applying on the desired hair area, a hair treating effective amount of at least one composition comprising hydrated lipidic lamellar phases or liposomes containing at least in part a component selected from a derivative of labdane of formula I herebelow:

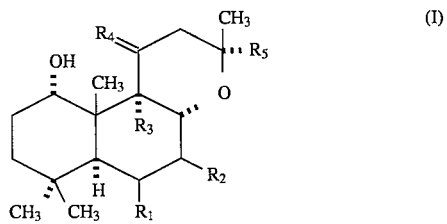

in which:

$R_1$ and $R_2$ are identical or different and each represent a hydroxy group or an —O—CO—$R_6$ group in which $R_6$ represents an alkyl radical having from 1 to 7 atoms of carbon, an alkoxy radical having from 1 to 7 atoms of carbon, or an alkenyl radical having from 1 to 7 atoms of carbon, optionally substituted by one or more hydroxy or

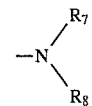

groups in which $R_7$ and $R_8$ each represent an atom of hydrogen, an alkyl radical having from 1 to 4 atoms of carbon or $R_7$ and $R_8$ represent together and with the atom of nitrogen, a heterocyclic radical such as piperidino, morpholino, N'-methylpiperazino;

$R_3$ represents an atom of hydrogen or a hydroxy group;

$R_4$ represents an atom of oxygen to the assembly

$R_5$ represents an ethyl or vinyl radical; optionally in a pharmaceutically or cosmetically acceptable excipient.

2. The method of claim 1, wherein the labdane derivative is a component of formula I in which:

$R_1$ represents the hydroxy group;

$R_2$ represents a hydroxy group or a —O—CO—$R_6$ group in which $R_6$ represents an alkyl radical having from 1 to 4 atoms of carbon, an alkoxy radical having from 1 to 4 atoms of carbon or an alkenyl radical having from 1 to 4 atoms of carbon, possibly substituted by one or two hydroxy groups or, at one chain end,

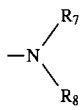

group in which $R_7$ and $R_8$ each represent a methyl or ethyl radical or represent together and with the neighboring atom of oxygen, a heterocyclic radical such as piperidino, morpholino, N'-methylpiperazino;

$R_3$ represents the hydroxy group, $R_4$ represents an atom of oxygen, $R_5$ represents the vinyl radical.

3. The method of claim 1, wherein said labdane derivative is selected from the group consisting of:

forskoline

7-O-deacetyl-forskoline coleforsine

7-O-deacetyl-7-β-O-propanoyl-forskokine

7-O-deacetyl-7-β-O-(ethoxycarbonyl)-forskoline

7-O-deacetyl-7-β-O-(propoxycarbonyl)-forskoline

7-O-deacetyl-7-β-O-(2,3-dihydroxy-propanoyl)-forskoline

7-O-deacetyl-7-β-O-(3-methyl-2-butenoyl)-forskoline

7-O-deacetyl-7-β-O-[4-(N'-methyl-piperazino)-butanoyl]-forskoline

7-O-deacetyl-7-β-O-(4-morpholino-butanoyl)-forskoline

6-β-O-[3-piperidino-propanoyl]-forskoline

6-β-O-(piperidino-acetyl)-forskoline.

4. The method of claim 1, wherein the concentration of said derivative of labdane incorporated at least in part in hydrated lipidic lamellar phases or liposomes is added at a level of between 0.0001% and 1% by weight with respect to the total weight of the composition.

5. The method of claim 1, wherein said composition contains a pigment promoting amount of at least one other active substance, selected from the group consisting of xanthines, tyrosine, tyrosine salts and tyrosine esters, said active substance being optionally incorporated at least in part in said hydrated lipidic lamellar phases or liposomes.

6. The method of claim 1, wherein said composition comprises liposomes.

7. The method of claim 1, wherein the concentration of said derivative of labdane incorporated at least in part in hydrated lipidic lamellar phases or liposomes in included at a level of between about 0.01% and 0.1% by weight, with respect to the total weight of the composition.

8. The method of claim 5, wherein said tyrosine ester is glucose tyrosinate.

9. The method of claim 1, wherein said composition further comprises theophylline.

10. A method for promoting hair pigmentation, comprising applying on the areas in need of said treatment, a treating efficient amount of at least one composition comprising hydrated lipidic lamellar phases or liposomes encapsulating a *Coleus forskolii* plant tissue extract obtained by extracting said *Coleus forskolii* plant with an organic solvent.

11. The method of claim 10, wherein said Coleus tissue extract is a root extract.

12. The method of claim 10, wherein said organic solvent is selected from the group consisting of an alkanol, a carboxylic acid, a carboxylic acid ester, a dialkyl ketone, a dialkyl ether, an aromatic hydrocarbon, a halogenated aliphatic hydrocarbon and a halogenated aromatic hydrocarbon.

13. The method of claim 10, wherein said alkanol is selected from the group consisting of methanol and ethanol; said aromatic hydrocarbon is selected from the group consisting of benzene, toluene and xylene; said halogenated aliphatic hydrocarbon is selected from the group consisting of methylene chloride and chloroform; said carboxylic acid ester is ethyl acetate.

14. The method of claim 10, wherein said solvent extraction is effected at a temperature ranging between the ambient temperature and the boiling point of the organic solvent; the ratio of the *Coleus forskolii* plant tissue with respect to the organic solvent is ranging between 1:5 and 1:20 part by weight.

15. The method of claim 10, wherein said extraction comprises an end extraction step with an alcohol.

16. The method of claim 15, wherein said alcohol is ethanol.

17. The method of claim 10, wherein said composition comprises from 0.0001% to 1% by weight, with respect to the total weight of the composition, of said *Coleus forskolii* extract.

18. The method of claim 10, wherein said composition comprises from 0.01% to 1% by weight, with respect to the total weight of the composition, of said *Coleus forskolii* extract.

19. The method of claim 10, wherein said composition comprises from 0.01% to 0.1% by weight, with respect to the total weight of the composition, of said *Coleus forskolii* extract.

20. The method of claim 10, wherein said composition comprises a cosmetically or pharmaceutically efficient amount of at least one other active substance selected from the group consisting of xanthines, tyrosine, and glucose tyrosinate, said active substance being optionally incorporated in hydrated lipidic lamellar phases or liposomes.

21. The method of claim 20, further comprising theophylline.

22. The method of claim 10, wherein said composition comprises theophylline and hydrated lipidic lamellar phases or liposomes containing said *Coleus forskolii* extract.

* * * * *